US009280825B2

(12) United States Patent
Huang et al.

(10) Patent No.: US 9,280,825 B2
(45) Date of Patent: Mar. 8, 2016

(54) IMAGE PROCESSING SYSTEM WITH REGISTRATION MECHANISM AND METHOD OF OPERATION THEREOF

(71) Applicant: Sony Corporation, Tokyo (JP)

(72) Inventors: Albert Huang, Cupertino, CA (US);
Ming-Chang Liu, San Jose, CA (US)

(73) Assignee: Sony Corporation, Tokyo (JP)

( * ) Notice: Subject to any disclaimer, the term of this patent is extended or adjusted under 35 U.S.C. 154(b) by 7 days.

(21) Appl. No.: 14/202,677

(22) Filed: Mar. 10, 2014

(65) Prior Publication Data

US 2015/0254857 A1    Sep. 10, 2015

(51) Int. Cl.
*G06K 9/00* (2006.01)
*G06T 7/00* (2006.01)

(52) U.S. Cl.
CPC ..... *G06T 7/0042* (2013.01); *G06T 2207/10028* (2013.01)

(58) Field of Classification Search
CPC ................... G06T 7/0042; G06T 3/60; G06T 2207/10028
See application file for complete search history.

(56) References Cited

U.S. PATENT DOCUMENTS

| | | | |
|---|---|---|---|
| 5,644,689 A * | 7/1997 | Ban et al. ....................... | 345/424 |
| 5,715,166 A * | 2/1998 | Besl et al. ...................... | 700/182 |
| 6,006,123 A * | 12/1999 | Nguyen et al. ................ | 600/374 |
| 7,647,087 B2 | 1/2010 | Miga et al. | |
| 8,145,012 B2 | 3/2012 | Meetz et al. | |
| 8,290,305 B2 | 10/2012 | Minear et al. | |
| 8,363,930 B1 | 1/2013 | Francis, Jr. et al. | |
| 8,416,240 B1 * | 4/2013 | Kuffner et al. ................ | 345/426 |
| 8,437,518 B2 | 5/2013 | Chan et al. | |
| 8,442,304 B2 * | 5/2013 | Marrion ............... | G06K 9/6211 382/154 |
| 8,774,504 B1 * | 7/2014 | Sundareswara et al. ...... | 382/165 |
| 8,948,501 B1 * | 2/2015 | Kim ...................... | G01S 7/4808 345/419 |
| 9,053,547 B2 * | 6/2015 | Kitamura et al. | |
| 2003/0067461 A1 * | 4/2003 | Fletcher et al. ............... | 345/420 |
| 2003/0231179 A1 * | 12/2003 | Suzuki ........................... | 345/423 |
| 2004/0047044 A1 * | 3/2004 | Dalton .......................... | 359/630 |
| 2005/0151963 A1 * | 7/2005 | Pulla et al. ............... | 356/139.03 |
| 2006/0020204 A1 | 1/2006 | Serra et al. | |
| 2007/0172129 A1 * | 7/2007 | Tortora et al. ................ | 382/218 |
| 2009/0104585 A1 | 4/2009 | Diangelo et al. | |

(Continued)

FOREIGN PATENT DOCUMENTS

WO    2009045827 A2    4/2009

OTHER PUBLICATIONS

U.S. Appl. No. 14/331,541, filed Jul. 15, 2014, Huang et al.

(Continued)

*Primary Examiner* — Gregory M Desire
(74) *Attorney, Agent, or Firm* — Ishimaru & Associates LLP

(57) ABSTRACT

An image processing system, and a method of operation thereof, including: a feature selection module for determining subsets of point clouds, the subsets selected based on key points of a three-dimensional object; a feature matching module, coupled to the feature selection module, for generating matched results based on a matching transformation of the subsets; and a point registration module, coupled to the feature matching module, for refining the matched results based on a refinement transformation to optionally align different data sets of the point clouds for displaying the aligned data sets on a device, wherein the refinement transformation includes a refinement error less than a matching error of the matching transformation.

20 Claims, 6 Drawing Sheets

(56) References Cited

U.S. PATENT DOCUMENTS

| | | | | |
|---|---|---|---|---|
| 2009/0171627 | A1* | 7/2009 | Olson | G06T 17/00 |
| | | | | 703/1 |
| 2010/0209005 | A1* | 8/2010 | Rudin | G06K 9/00214 |
| | | | | 382/218 |
| 2012/0294534 | A1* | 11/2012 | Watanabe et al. | 382/195 |
| 2013/0004060 | A1 | 1/2013 | Bell et al. | |
| 2013/0051658 | A1* | 2/2013 | Hwang et al. | 382/154 |
| 2013/0123792 | A1 | 5/2013 | Fitz et al. | |
| 2015/0003723 | A1* | 1/2015 | Huang | G06K 9/6212 |
| | | | | 382/154 |

OTHER PUBLICATIONS

BRAINLAB, ElectroMagnetic ENT Navigation, Intuitive Power, 2011, pp. 8 Publisher: BrainLab NS-FL-E-CRANIAL NAV-0511 Q: 2,000, Published in: Germany.

GE_HEALTHCARE, Integration with GE Insta Trak 3500 Plus, GE Healthcare, 2010, pp. 1 Publisher: GE.

MEDTRONIC, Fusion ENT Navigation System for Image-Guided Surgery, Jan. 9, 2013, pp. 2 Publisher: Medtronic.

STRYKER Intellect Cranial Navigation System, 2006, pp. 2.

WATERWORTH, Virtual Reality in Medicine, 3 Medical VR:the main application areas and what has been done, 1999, pp. 25 Publisher: Department of Informatik, Published in: Sweden.

Papalazarou et al., "Sparse-plus-dense-RANSAC for estimation of multiple complex curvilinear models in 2D and 3D", "Pattern Recognition", Sep. 25, 2012, pp. 925935, vol. 46 Elsevier, The Netherlands.

Sielhorst et al., "Advanced Medical Displays: A Literature Review of Augmented Reality", "Journal of Display Technology", Dec. 2008, p. 451-467, vol. 4, No. 4, IEEE.

\* cited by examiner

IMAGE PROCESSING SYSTEM WITH REGISTRATION MECHANISM AND METHOD OF OPERATION THEREOF

TECHNICAL FIELD

The present invention relates generally to an image processing system, and more particularly to a system for an image processing with registration.

BACKGROUND ART

In imaging science, image processing is any form of signal processing for which the input is an image, such as a photograph or a video frame; the output of image processing may be either an image or a set of characteristics or parameters related to the image. Most image-processing techniques involve treating the image as a two-dimensional (2D) signal and applying standard signal-processing techniques to it.

Image processing usually refers to digital image processing, but optical and analog image processing also are possible. The acquisition of images is referred to as imaging. Image processing refers to processing of a 2D picture by a computer. An image defined in the "real world" is considered to be a function of two real variables, for example, a(x,y) with a as the amplitude (e.g., brightness) of the image at the real coordinate position (x,y).

Modern digital technology has made it possible to manipulate multi-dimensional signals with systems that range from simple digital circuits to advanced parallel computers. The goal of this manipulation can be divided into three categories of Image Processing (image in ->image out), Image Analysis (image in ->measurements out), and Image Understanding (image in ->high-level description out).

An image may be considered to contain sub-images sometimes referred to as regions-of-interest, ROIs, or simply regions. This concept reflects the fact that images frequently contain collections of objects, each of which can be the basis for a region. In a sophisticated image processing system, it should be possible to apply specific image processing operations to selected regions. Thus, one part of an image (region) might be processed to suppress motion blur while another part might be processed to improve color rendition.

Most usually, image processing systems require that the images be available in digitized form, that is, arrays of finite length binary words. For digitization, the given Image is sampled on a discrete grid and each sample or pixel is quantized using a finite number of bits. The digitized image is processed by a computer. To display a digital image, it is first converted into analog signal, which is scanned onto a display.

Closely related to image processing are computer graphics and computer vision. In computer graphics, images are manually made from physical models of objects, environments, and lighting, instead of being acquired (via imaging devices such as cameras) from natural scenes, as in most animated movies. Computer vision, on the other hand, is often considered high-level image processing, out of which a machine/computer/software intends to decipher the physical contents of an image or a sequence of images (e.g., videos or three-dimensional (3D) full-body magnetic resonance scans).

In modern sciences and technologies, images also gain much broader scopes due to the ever-growing importance of scientific visualization (of often large-scale complex scientific/experimental data). Examples include microarray data in genetic research or real-time multi-asset portfolio trading in finance.

Thus, a need still remains for an image processing system to be developed. In view of the ever-increasing commercial competitive pressures, along with growing consumer expectations, it is critical that answers be found for these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

The present invention provides a method of operation of an image processing system that includes determining subsets of point clouds, the subsets selected based on key points of a three-dimensional object; generating matched results based on a matching transformation of the subsets; and refining the matched results based on a refinement transformation to align different data sets of the point clouds for displaying the aligned data sets on a device, wherein the refinement transformation includes a refinement error less than a matching error of the matching transformation.

The present invention provides an image processing system that includes a feature selection module for determining subsets of point clouds, the subsets selected based on key points of a three-dimensional object; a feature matching module, coupled to the feature selection module, for generating matched results based on a matching transformation of the subsets; and a point registration module, coupled to the feature matching module, for refining the matched results based on a refinement transformation to align different data sets of the point clouds for displaying the aligned data sets on a device, wherein the refinement transformation includes a refinement error less than a matching error of the matching transformation.

Certain embodiments of the invention have other steps or elements in addition to or in place of those mentioned above. The steps or the elements will become apparent to those skilled in the art from a reading of the following detailed description when taken with reference to the accompanying drawings.

BEST MODE FOR CARRYING OUT THE INVENTION

Figure 1:
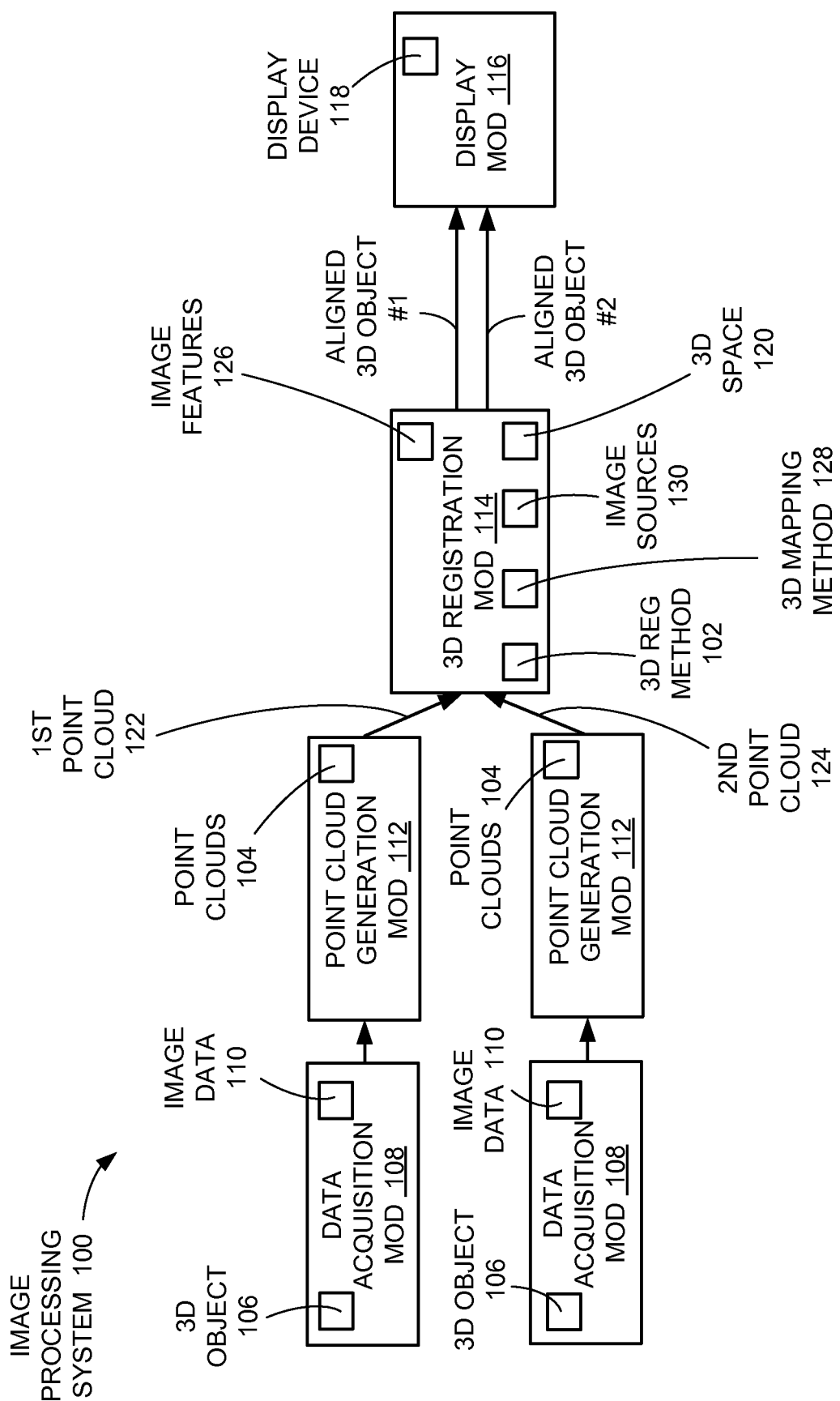
FIG. 1 is a system diagram of an image processing system with registration mechanism in an embodiment of the present invention.

The following embodiments are described in sufficient detail to enable those skilled in the art to make and use the invention. It is to be understood that other embodiments would be evident based on the present disclosure, and that system, process, or mechanical changes may be made without departing from the scope of the present invention.

In the following description, numerous specific details are given to provide a thorough understanding of the invention. However, it will be apparent that the invention may be practiced without these specific details. In order to avoid obscuring the present invention, some well-known circuits, system configurations, and process steps are not disclosed in detail.

The drawings showing embodiments of the system are semi-diagrammatic and not to scale and, particularly, some of the dimensions are for the clarity of presentation and are shown exaggerated in the drawing FIGS. Similarly, although the views in the drawings for ease of description generally show similar orientations, this depiction in the FIGS. is arbitrary for the most part. Generally, the invention can be operated in any orientation.

Where multiple embodiments are disclosed and described having some features in common, for clarity and ease of illustration, description, and comprehension thereof, similar and like features one to another will ordinarily be described with similar reference numerals. The embodiments have been numbered first embodiment, second embodiment, etc. as a matter of descriptive convenience and are not intended to have any other significance or provide limitations for the present invention.

The term "module" referred to herein can include software, hardware, or a combination thereof in the present invention in accordance with the context in which the term is used. For example, the software can be machine code, firmware, embedded code, and application software. Also for example, the hardware can be circuitry, processor, computer, integrated circuit, integrated circuit cores, a microelectromechanical system (MEMS), passive devices, environmental sensors including temperature sensors, or a combination thereof.

Image processing can relate to projective imaging and tomographic imaging using imagers. The projective imaging employs planar view of an object using a camera and X-ray, as examples. The tomographic imaging employs slicing through an object using penetrating waves including sonar, computed tomography (CT) scan, magnetic resonance imaging (MRI), as examples.

Image data acquisition can include dense acquisition and sparse acquisition methods. The dense acquisition method can directly reconstruct a 3D object from 2D images. The sparse acquisition method is employed when not all image data are available due to time constraints. Each 2D image can require user interpretation on its spatial relevancy in a 3D space.

Object shapes can include a complete shape and a partial shape. The complete shape can include a 3D view of an object. The complete shape can be generated using 3D scanning and shape models, as examples. The partial shape can be generated when not all data are available due to occlusion and obstructed view, as examples. The partial shape can be generated using stereo, 2D scanning, as examples.

If sparse tomographic 2D images are acquired or partial 3D surfaces are obtained, a field of view is quite limited to only particular 2D image slices or 3D sections. Without knowing the relevancy of these sub-images with respect to a 3D object, significant user interpretations are required to understand the spatial correspondence of any 2D or 3D image features in a real world 3D space.

A dense 2D/3D image acquisition is performed to allow for a full 3D reconstruction of an object. This approach requires careful planning of an image acquisition sequence and an image stitching to form a complete 3D representation. However, if time or space permits only a sparse 2D or a partial 3D image acquisition to be performed, 3D object reconstruction may not be feasible due to missing intermediate data.

Referring now to FIG. 1, therein is shown a system diagram of an image processing system 100 with registration mechanism in an embodiment of the present invention. The image processing system 100 includes a three-dimensional registration method 102 using point clouds 104. The term "point" referred to herein is a data value and/or a coordinate in the point clouds 104.

The point clouds 104 are sets of 3D points and/or coordinates. The point clouds 104 are collected from 3D images. For example, the point clouds 104 can be a set of points around or at a surface of a three-dimensional object 106 of interest. As a specific example, the point clouds 104 can be acquired based on ultrasound data of the three-dimensional object 106.

The image processing system 100 includes data acquisition modules 108 for acquiring or obtaining image data 110 of the three-dimensional object 106. The image data 110 include 2D or 3D information related to the three-dimensional object 106 of interest. The image processing system 100 includes point cloud generation modules 112 for generating the point clouds 104 based on the image data 110.

The image processing system 100 includes a three-dimensional registration module 114 for employing the shape feature selection, matching, and optimization algorithms, which will subsequently be described in more details in FIGS. 4-5. The image processing system 100 can include a display module 116 for analyzing and displaying the point clouds 104 or relevant data, that have been aligned by the three-dimensional registration module 114, on a display device 118, which is an equipment including hardware for presenting information.

The image processing system 100 generates one of the point clouds 104 in a three-dimensional space 120 and matches with another of the point clouds 104 in the three-dimensional space 120. The one of the point clouds 104 can be a first point cloud 122 from one of the point cloud generation modules 112, and the another of the point clouds 104 can be a second point cloud 124 from another of the point cloud generation modules 112. The first point cloud 122 and the second point cloud 124 can be 3D point clouds.

A novelty of the image processing system 100 is that by using the three-dimensional registration method 102 between two of the point clouds 104 in the three-dimensional space 120, corresponding image features 126 are easily mapped between each other. The image features 126 include sparse 2D or partial 3D features of the three-dimensional object 106.

The novelty of the image processing system 100 is a three-dimensional mapping method 128 between data of the point clouds 104 from various image sources 130, which will subsequently be described in FIG. 2. The three-dimensional mapping method 128 can be employed for structural mapping.

Another novelty of the image processing system 100 is that it extracts and matches only on the image features 126 including significant surface features. This allows an image registration method or the three-dimensional registration method 102, which is fast and robust without requiring initialization, to be or close to an optimal solution. Potential application areas for the image processing system 100 include but not limit to security screening, biomedical imaging, archaeological exploration, object tracking in robotics, face matching, and alignment of range images for environment modeling.

Therefore, the main idea of the image processing system 100 is that the point clouds 104 having two different data sets of the three-dimensional object 106 or the same object are generated. However, the point clouds 104 are generated in different coordinate states. These two data sets are aligned in the three-dimensional space 120 by employing shape feature selection, matching, and optimization algorithms, which will subsequently be described in FIGS. 4-6.

With regard to what kind of data in the data sets, the point clouds 104 are generated or obtained in the three-dimensional space 120. For example, the point clouds 104 can include the first point cloud 122 from a complete data set of 2D or 3D images of a person's head. In addition, the point clouds 104 can include the second point cloud 124 from a partial data set of 2D or 3D images taken by a different imaging device at a different time. Then, the first point cloud 122 and the second point cloud 124 are aligned with each other so that both data sets are processed together.

It has been found that the image processing system 100 solves a problem of taking the data sets of the point clouds 104 in two unknown dimensional spaces and then automatically aligned 3D objects by aligning the corresponding point clouds 104 together without any human intervention or human effort.

Figure 2:
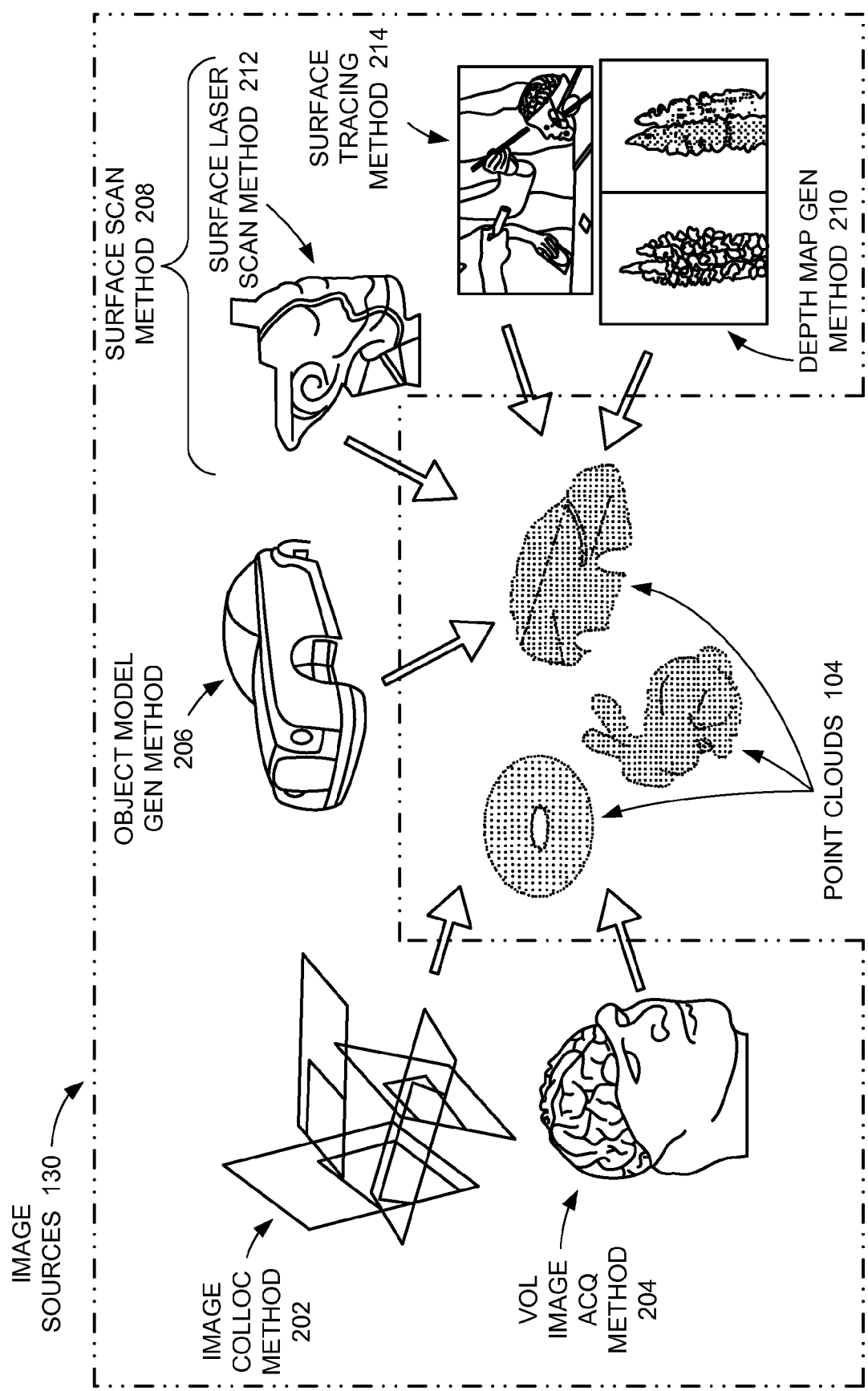
FIG. 2 is an exemplary block diagram of the image sources in the image processing system of FIG. 1.

Referring now to FIG. 2, therein is shown an exemplary block diagram of the image sources 130 in the image processing system 100 of FIG. 1. The point clouds 104 can be generated or derived potentially by any number of the image sources 130.

As an example, the point clouds 104 can be generated based on the image sources 130 using an image collocation method 202. The image collocation method 202 can be employed for object surface segmentation of the three-dimensional object 106 of FIG. 1. The image collocation method 202 can be used for obtaining sparsely acquired 2D images or 3D collocated images.

As another example, the point clouds 104 can be generated based on the image sources 130 using a volumetric image acquisition method 204. The volumetric image acquisition method 204 can be employed for obtaining a 3D volumetric image or a rendered surface of the three-dimensional object 106.

As a further example, the point clouds 104 can be generated based on the image sources 130 using an object model generation method 206. The object model generation method 206 can be employed for obtaining a 3D object surface model or a 3D shape model of the three-dimensional object 106.

As a yet further example, the point clouds 104 can be generated based on the image sources 130 using a surface scanning method 208. The surface scanning method 208 can be employed for obtaining a depth map generation method 210. The surface scanning method 208 can include a surface laser scanning method 212 and a surface tracing method 214.

The depth map generation method 210 generates depth information associated with the three-dimensional object 106. The depth map generation method 210 can be employed for generating the depth information or a depth image using by a stereo imaging process. The depth information can be generated by a structured-light 3D scanner or device that measures a three-dimensional shape of the three-dimensional object 106 using projected light patterns and a camera system.

The surface laser scanning method 212 is employed to obtain 2D or 3D images. For example, the 2D images can include sparsely acquired 2D images of the three-dimensional object 106. Also for example, the 3D images can include collocated 3D images or 2D partial views of the three-dimensional object 106. Further, for example, the 3D images can provide 3D full views of the three-dimensional object 106.

The surface tracing method 214 is employed to obtain surface information of the three-dimensional object 106. The surface tracing method 214 can be performed using sensors or markers. For example, the surface tracing method 214 can be performed using tracked instruments.

Figure 3:
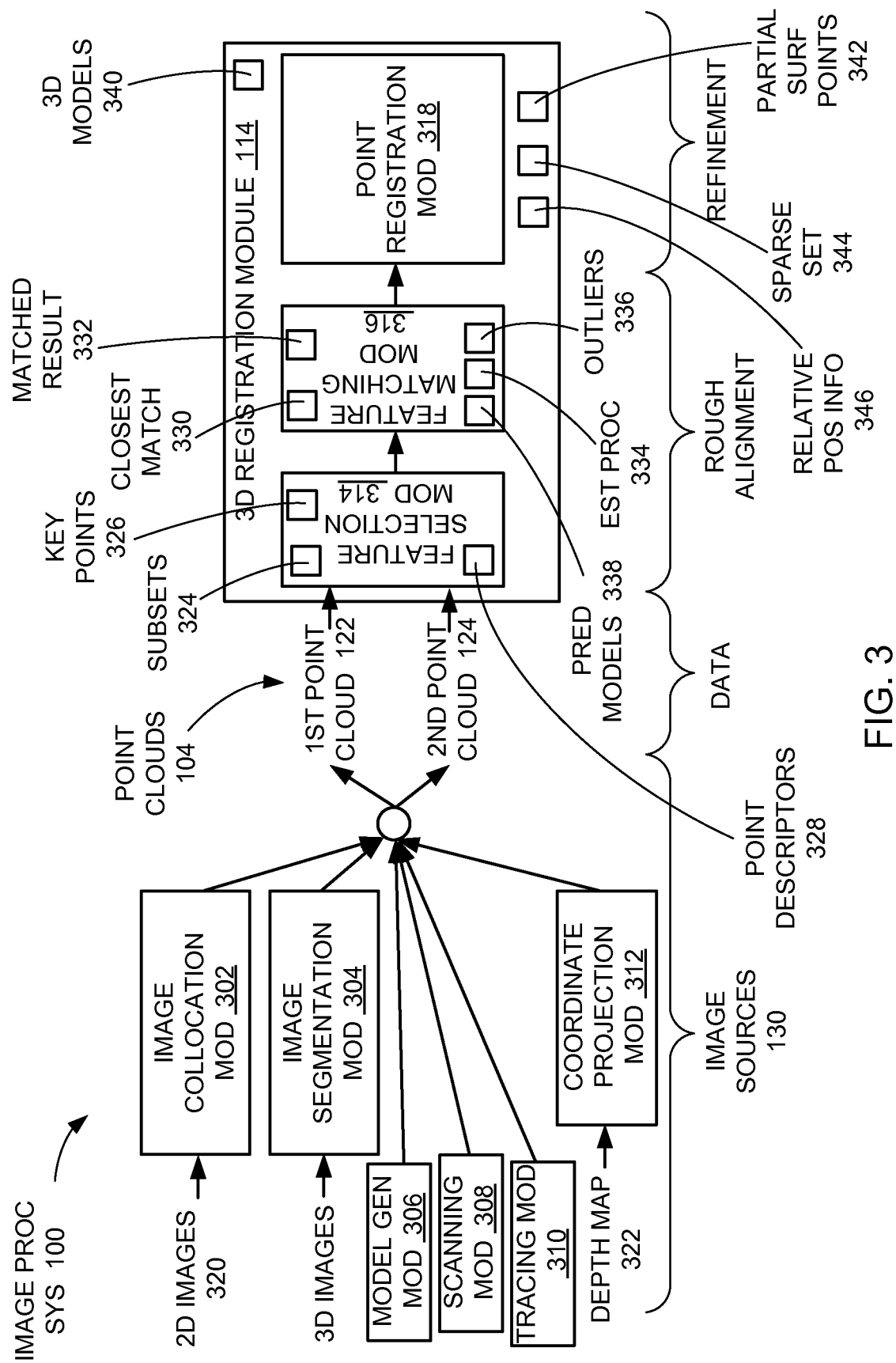
FIG. 3 is a detailed block diagram of the image processing system.

Referring now to FIG. 3, therein is shown a detailed block diagram of the image processing system 100. The image processing system 100 can include an image collocation module 302, an image segmentation module 304, a model generation module 306, a scanning module 308, a tracing module 310, and/or a coordinate projection module 312.

The image collocation module 302, the image segmentation module 304, the model generation module 306, the scanning module 308, the tracing module 310, and the coordinate projection module 312 can provide the image sources 130 or data sources associated with the three-dimensional object 106 of FIG. 1. The image sources 130 are used to determine the first point cloud 122 and the second point cloud 124 as data provided to the three-dimensional registration module 114.

The image collocation module 302, the image segmentation module 304, and the model generation module 306 include the image collocation method 202 of FIG. 2, the volumetric image acquisition method 204 of FIG. 2, and the object model generation method 206 of FIG. 2, respectively. The scanning module 308, the tracing module 310, and the coordinate projection module 312 include the surface laser scanning method 212 of FIG. 2, the surface tracing method 214 of FIG. 2, and the depth map generation method 210 of FIG. 2, respectively.

The three-dimensional registration module 114 includes a feature selection module 314, a feature matching module 316, and a point registration module 318. The feature selection module 314 is coupled to the feature matching module 316. The feature matching module 316 is coupled to the point registration module 318.

The feature selection module 314 and the feature matching module 316 perform an alignment for the three-dimensional object 106 of interest based on the first point cloud 122 and the second point cloud 124. The point registration module 318 can perform refinement, as needed, to further align the first point cloud 122 and the second point cloud 124.

The image collocation module 302 determines positions of a set of two-dimensional images 320 in their corresponding locations in the three-dimensional space 120 of FIG. 1. For example, during an ultrasound scanning process of a spinal cord, each of the two-dimensional images 320 is generated for each ultrasound scan along the spinal cord. As a result, a 3D image, of the three-dimensional object 106 as the spinal cord in this example, can be constructed based on the set of the two-dimensional images 320 in their corresponding locations in the three-dimensional space 120.

The image segmentation module 304 determines portions of the three-dimensional object 106 so that the feature selection module 314 and the feature matching module 316 perform just those portions instead of the entire dense analysis, which requires extensive computation resources and time. For example, the portions of the three-dimensional object 106 can include segments of a surface of the three-dimensional object 106 using ultrasound.

The coordinate projection module 312 converts coordinates from a depth map 322 to real world coordinates in the three-dimensional space 120. For example, a set of the 3D images is acquired by the stereo imaging process or two-camera systems, and a location or a coordinate of each point of pixels in the 3D images can essentially be calculated in the three-dimensional space 120. In this example, the coordinate projection module 312 simply converts coordinates from a stereo imaging system to the real world coordinates in the three-dimensional space 120.

An idea of the image processing system 100 is that the point clouds 104 can be generated from difference sources or the image sources 130. For example, the point clouds 104 can be generated using the image collocation method 202 from a set of 2D images that are collocated in their appropriate spaces. As a particular example, the image sources 130 can be acquired using an ultrasound process to generate 2D ultrasound images. Then, sources of the 2D ultrasound images are tracked and used to construct 3D images in the three-dimensional space 120. The point clouds 104 are generated based on the 3D images.

As a specific example, the point clouds 104 can represent a tissue of a spinal cord of interest. A series of the 2D ultrasound images can be acquired to obtain the point clouds 104 around the spinal cord to generate the point clouds 104 in the three-dimensional space 120.

Also for example, the point clouds 104 can be generated from MRI or CT scan using the image collocation method 202. Further, for example, the point clouds 104 can be generated from a 3D computer graphics model using the object model generation method 206. As a specific example, the point clouds 104 can be generated based on vertices of a mesh model of a car. As another specific example, the surface laser scanning method 212 can be used to generate the mesh model, from which the vertices are used to generate the point clouds 104.

Further, for example, the point clouds 104 can be generated from a depth map space using the depth map generation method 210 with the stereo imaging process or the structured-light 3D scanner to construct 3D information of the three-dimensional object 106 of interest. The 3D information is used to calculate coordinates of the three-dimensional object 106 in the three-dimensional space 120 to generate the point clouds 104.

The point clouds 104 are generated without any restrictions on the image sources 130. In other words, any combination of the image sources 130 can be used to generate the point clouds 104, such as the first point cloud 122 and the second point cloud 124.

The feature selection module 314 determines subsets 324 of the point clouds 104 for subsequent processing. The subsets 324 are selected for each of the first point cloud 122 and the second point cloud 124.

The subsets 324 are selected based on key points 326, which are pre-determined specific shaped features, landmarks, or physical characteristics of the three-dimensional object 106. The key points 326 are automatically determined by the feature selection module 314 to perform the alignment between the first point cloud 122 and the second point cloud 124.

A set of the key points 326 is extracted from the first point cloud 122. Point descriptors 328 are calculated for the key points 326 based on their neighbors. This process is repeated for the second point cloud 124. The point descriptors 328 are stored information used to identify the three-dimensional object 106 of interest. For example, the point descriptors 328 can identify a shape, a landmark, or any other features or physical characteristics of the three-dimensional object 106.

The feature matching module 316 compares and matches the point descriptors 328 of the point clouds 104. The feature matching module 316 determines a closest match 330 to determine a matched result 332 between the point descriptors 328 of the point clouds 104 including the first point cloud 122 and the point descriptors 328 of the second point cloud 124.

The feature matching module 316 employs an estimation process 334 that determines the closest match 330 between the point descriptors 328 of the first point cloud 122 and the point descriptors 328 of the second point cloud 124. The estimation process 334 can include a method of removing outliers 336 that do not fit predetermined models 338 of the three-dimensional object 106 of interest.

For example, once the closest match 330 is determined, the feature matching module 316 can employ a random sample consensus (RANSAC) algorithm based on the predetermined models 338, which are based on a physical structure of the three-dimensional object 106. The RANSAC algorithm is used to remove outlying matches that do not fit rotation, translation, or other transformation assumptions.

The RANSAC algorithm is an iterative method to estimate parameters of a mathematical model from a set of observed data, which contains the outliers 336. It is a non-deterministic algorithm in a sense that it produces a reasonable result only with a certain probability, with this probability increasing as more iteration is performed.

Once the alignment is complete by the feature selection module 314 and the feature matching module 316, the point registration module 318 is employed to optionally fine-tune the results of the feature matching module 316. A refinement process is employed to fine-tune the results. The refinement process can include a mathematical function to minimize distances between the point clouds 104 to further improve alignment of data from the first point cloud 122 and the second point cloud 124.

By using a three-dimensional model 340 as the reference, the image processing system 100 allows the three-dimensional mapping method 128 of FIG. 1 to include spatial mapping of partial surface points 342 derived from sparsely 2D or partial 3D images, via registration. The three-dimensional mapping method 128 is fast because only the partial surface points 342 with the significant surface features are used. The partial surface points 342 are information or coordinates of portions at a surface of the three-dimensional object 106.

The three-dimensional mapping method 128 is robust because feature correspondence eliminates the need for good initialization. Once the partial surface points 342 are registered, structural correspondence of the significant surface features in the sparse 2D or partial 3D images of the first point cloud 122 can directly relate to the second point cloud 124 of the three-dimensional object 106 in the three-dimensional space 120.

The image processing system 100 can be used in contexts where 2D tomographic images are available, and the three-dimensional object 106 of interest has a distinct known shape, such as detection of weaponry in security screening, visualization of anatomy in biomedical images, and identification of relics in archaeological exploration, as examples. The image processing system 100 can also be used in contexts where two sets of 3D shape data are available, and a geometric alignment is unknown, such as object tracking in robotics, face matching, and alignment of range images for environment modeling, as examples.

If a sparse set 344 of the two-dimensional images 320 of the three-dimensional object 106 is acquired and relative position information 346 for each of the 2D images is available, the point clouds 104 of the image features 126 of FIG. 1 of the three-dimensional object 106 can be extracted. The relative position information 346 can be available via any position acquisition methods including collocation or external sensors. The point clouds 104 can include 3D point clouds. The image features 126 can include surface features of the three-dimensional object 106.

If the sparse set 344 of the two-dimensional images 320 with the partial surface points 342 is already acquired in the three-dimensional space 120, the point clouds 104 can be used directly. Then, the point clouds 104 extracted for the image features 126 can be registered using the three-dimensional registration method 102 of FIG. 1 with the second point cloud 124 of the three-dimensional object 106 of interest through feature correspondence and function optimization, which will subsequently be described in FIGS. 5 and 6, respectively.

It has been found that the subsets 324 selected based on the key points 326 of the three-dimensional object 106 provide an advantage of significant reduction of computation efforts.

Figure 4:
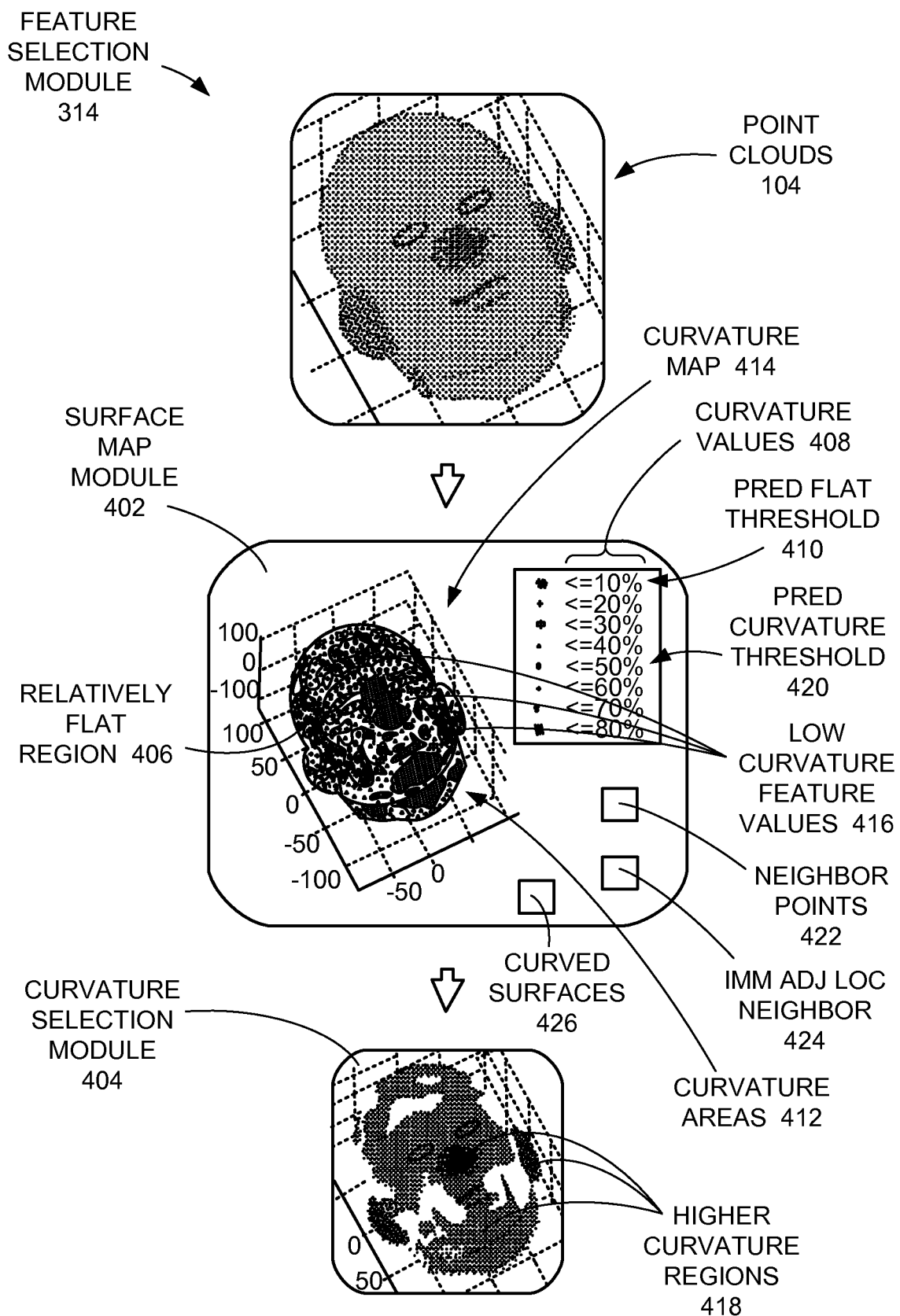
FIG. 4 is an exemplary block diagram of the feature selection module.

Referring now to FIG. 4, therein is shown an exemplary block diagram of the feature selection module 314. The feature selection module 314 performs a 3D feature selection of the image features 126 of FIG. 1 from the point clouds 104. The feature selection module 314 can include a surface map module 402 and a curvature selection module 404. For illustrative purposes, FIG. 4 includes hatching patterns to show curvature areas 412 having different curvature values 408.

A purpose of the feature selection module 314 is to significantly reduce an amount of matching needed thereby reducing computational resources and time resulting in improved performance without sacrificing accuracy. The amount of the matching is significantly reduced by ignoring or filtering out relatively flat regions 406 with no significant features that would otherwise generate false matching subsequently processed by the feature matching module 316 of FIG. 3.

The relatively flat regions 406 are surfaces having the curvature values 408 less than or equal to a predetermined flat threshold 410. For example, the predetermined flat threshold 410 can be equal to 10%.

For illustration purposes, the curvature values 408 are described in terms of percentages. The curvature values 408 having numerical values of 0% represent the curvature areas 412 that are flat or having no curvature. The curvature values 408 having numerical values of 100% represent the curvature areas 412 that have the highest curvature among the point clouds 104 that are provided to the feature selection module 314 from the image sources 130 of FIG. 1 for detecting the three-dimensional object 106 of FIG. 1 of interest.

The surface map module 402 receives the point clouds 104 and generates a curvature map 414 based on the point clouds 104. The curvature map 414 is a map or a representation of a number of the curvature areas 412 based on the point clouds 104. The curvature map 414 shows the curvature areas 412 having different values for the curvature values 408. The curvature values 408 of local surfaces are estimated by fitting the point clouds 104 with curved surfaces 426.

The curvature selection module 404 removes the point clouds 104 with low curvature feature values 416 or the relatively flat regions 406. After the low curvature feature values 416 or the relatively flat regions 406 are removed, only higher curvature regions 418 remain. The higher curvature regions 418 are the subsets 324 of FIG. 3 of the point clouds 104. The higher curvature regions 418 are keep as they include key features or the key points 326 of FIG. 3.

The low curvature feature values 416 are the curvature values 408 less than or equal to a predetermined curvature threshold 420. The higher curvature regions 418 are the curvature values 408 greater than or equal to the predetermined curvature threshold 420.

The predetermined curvature threshold 420 and the predetermined flat threshold 410 are assigned to numerical values, to which the curvature values are compared to properly predict or estimate the three-dimensional object 106 without false matching of the point clouds 104. For example, the predetermined curvature threshold 420 can be equal to 50%.

The feature selection module 314 can select the image features 126 by employing other selection methods. The selection methods can possibly include other one-dimensional (1D) functions including distance, angle, area, and chord length. The selection methods can also include polygonal approximation and spatial features including convex hull, bounding box, and decomposition. The selection methods can further include moments or transforms using Fourier transforms, wavelet transforms, and shapelet transforms, or any other shape representations and combinations.

The curvature values 408 are calculated based on the point clouds 104 and neighbor points 422. Each of the point clouds 104 is surrounded by any number of the neighbor points 422 that defines an immediately adjacent local neighborhood 424. One of the curvature values 408 is calculated for one of the point clouds 104 with respect to the immediately adjacent local neighborhood 424 around one of the point clouds 104.

For example, consider taking a radius around a point from the point clouds 104 of a head that is shown in FIG. 4. As a specific example, the radius can be 2 centimeters or any other numerical values. Then, the curvature values 408 are estimated at specific points of the point clouds 104. Because the point clouds 104 are in the three-dimensional space 120 of FIG. 1, the curved surfaces 426 are generated through the point clouds 104 in order to calculate the curvature values 408.

Figure 5:
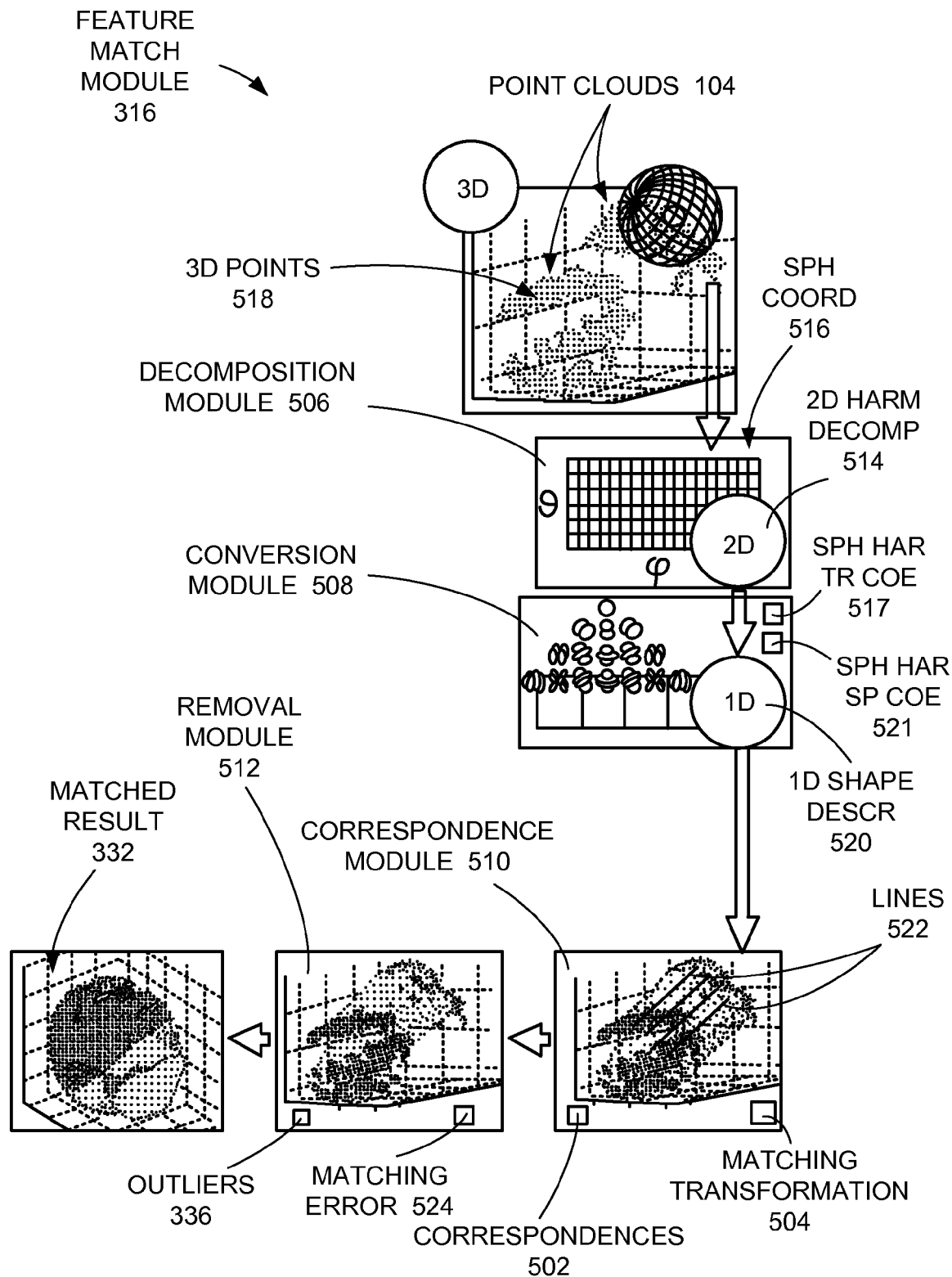
FIG. 5 is an exemplary block diagram of the feature matching module.

Referring now to FIG. 5, therein is shown an exemplary block diagram of the feature matching module 316. The feature matching module 316 performs a 3D feature matching based on the image features 126 of FIG. 1 from the point clouds 104.

A purpose of the feature matching module 316 is to find or determine correspondences 502 between feature or structural point pairs of the first point cloud 122 of FIG. 1 and the second point cloud 124 of FIG. 1 to establish a matching transformation 504 for point matching. The feature matching module 316 includes a decomposition module 506, a conversion module 508, a correspondence module 510, and a removal module 512.

The matching transformation 504 refers to a translation transformation, a rotation transformation, a scaling transformation, a spherical transformation, or a combination thereof employed in a process of matching the first point cloud 122 and the second point cloud 124. The matching transformation 504 is performed only for the key points 326 of FIG. 3 in each of the first point cloud 122 and the second point cloud 124.

Examples of the point clouds 104 are depicted in the top-right corner of FIG. 5. The decomposition module 506 can be implemented with a two-dimensional harmonic decomposition 514 of the point clouds 104 based on a two-dimensional histogram of spherical coordinates 516 between the points in the point clouds 104.

After the decomposition module 506 completes, the conversion module 508 converts spherical harmonic transform coefficients 517 of a shape as described by a locus of three-dimensional points 518 in the point clouds 104 into one-dimensional shape descriptors 520 as spherical harmonic spectrum coefficients 521 in by the decomposition module 506. A spherical harmonic decomposition takes a 2D map of the spherical coordinates 516 as an image and decomposes the map with spherical basis functions into coefficient values to represent the 2D image similar to fast Fourier transform (FFT) or discrete cosine transform (DCT). For example, the spherical basis functions can be generated by Legendre polynomials.

The one-dimensional shape descriptors 520 are calculated for each point in each of the first point cloud 122 and the second point cloud 124. The one-dimensional shape descriptors 520 can be employed for one-dimensional rotationally invariant shape descriptors.

The spherical coordinates 516 can be first accumulated into a histogram representing two angular components of a spherical coordinate system with the spherical coordinates 516. The histogram can then be decomposed into spherical harmonic coefficients including the spherical harmonic transform coefficients 517. The spherical harmonic coefficients can then be transformed into spectrum coefficients including the spherical harmonic spectrum coefficients 521, which are 1D representation of a spherical coordinate histogram. When an object rotates or translates, its local point cloud configuration remains the same; thus, producing the same 1D spectrum coefficients as if the object has not been rotated or translated.

Final values of 1D spectrum coefficients or the spherical harmonic spectrum coefficients 521 describe the shape as represented by local point clouds. Therefore, they are termed spherical harmonic shape descriptors.

After the conversion module 508 completes, the correspondence module 510 finds or determines the correspondences 502 between the point clouds 104 by descriptor matching based on the one-dimensional shape descriptors 520. The correspondence module 510 determines the correspondences 502 based on a sum of absolute differences between the one-dimensional shape descriptors 520.

The correspondence module 510 determines the correspondences 502 by detecting matches between points in the first point cloud 122 to points in the second point cloud 124. The correspondence module 510 matches points in the first point cloud 122 to points in the second point cloud 124. Lines 522 represent these point-to-point correspondences.

After the correspondence module 510 completes, the removal module 512 removes the outliers 336 by using an outlying match removal process including transformations based on the RANSAC algorithm. The removal module 512 then generates the matched result 332, which identifies a portion of the first point cloud 122 that matches another portion of the second point cloud 124.

The removal module 512 reduces a number of point-to-point correspondences to improve accuracy of determining the matched result 332. As an example, there can be 10,000 points in the point clouds 104, which can be reduced by the removal module 512 to identify only 20 true point-to-point correspondences, based on which the matching transformation 504 can be calculated. Applying the matching transformation 504 or its inverse to the first point cloud 122 or the second point cloud 124 can align the first point cloud 122 to the second point cloud 124 as accurate as the true point-to-point correspondences can be calculated.

For example, the feature matching module 316 can include other possible implementations for the 3D feature matching including identified landmark points, manual or semi-automatic alignment, and shape context matching. Also for example, the feature matching module 316 can include other possible implementations for the 3D feature matching inner distance matching and matching of other shape descriptors.

The alignment previously described in FIG. 3 represents the matching transformation 504 of the point clouds 104. The matching transformation 504 can be implemented because the point clouds 104 can have unknown orientations in the three-dimensional space 120 of FIG. 1.

The matching transformation 504 can include a matching error 524. For example, the matching error 524 can include a mean square error (MSE) approximately greater than or equal to 2 millimeters (mm) and approximately less than or equal to 5 mm depending on applications and depending on a performance of the feature matching module 316. As a specific example, the matching error 524 can include an MSE of 2.0014 mm.

After an initial transformation or the matching transformation 504 is applied to one of the point clouds 104, the matching error 524 can be calculated by taking all points from one of the point clouds 104 and finding closest or shortest distances for each of the points to points on the surfaces of the second point cloud 124. Values of the closest distances are then squared and averaged.

It has been found that the matched result 332 generated based on the matching transformation 504 provides good or improved performance because the matching transformation 504 is performed only for the key points 326, thereby significant computation reduction.

It has also been found that the matching transformation 504 can have a mean square error approximately greater than or equal to 2 mm and approximately less than or equal to 5 mm providing improved accuracy in alignment among the point clouds 104.

Figure 6:
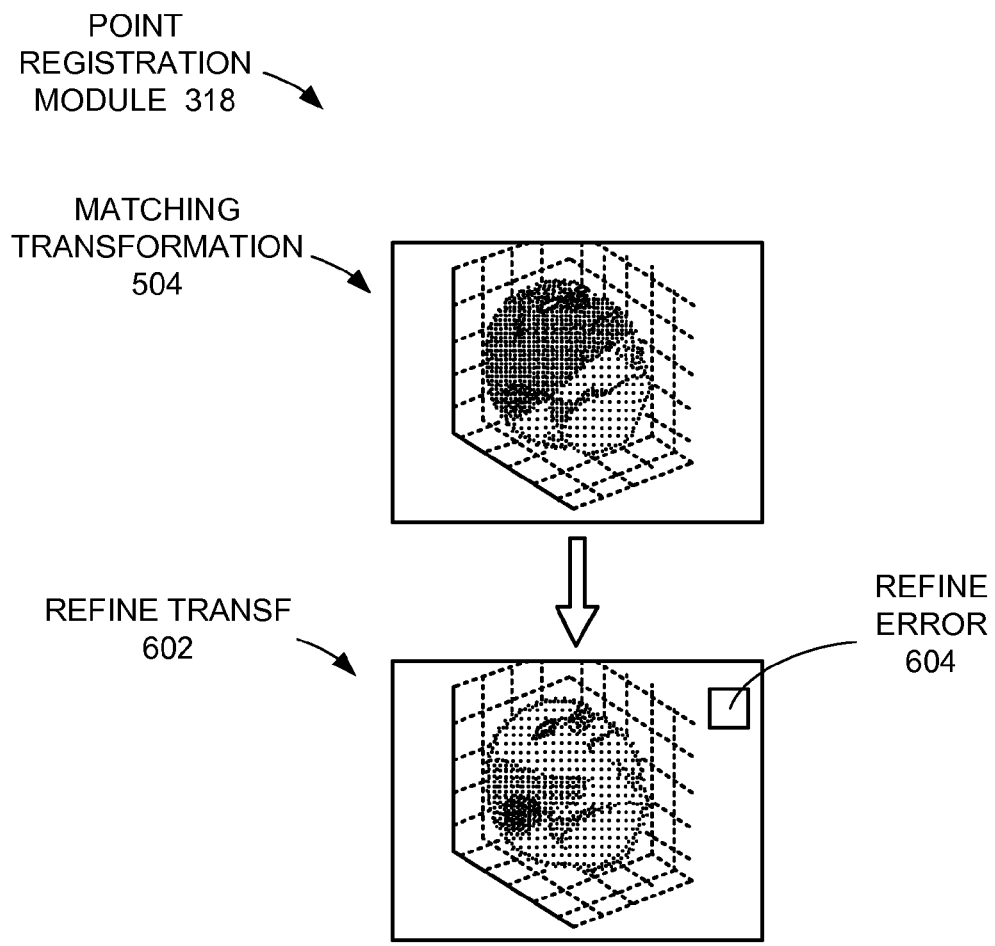
FIG. 6 is an exemplary block diagram of the point registration module.

Referring now to FIG. 6, therein is shown an exemplary block diagram of the point registration module 318. The point registration module 318 performs a 3D point registration based on a refinement transformation 602 using the matching transformation 504 from the feature matching module 316 of FIG. 3.

A purpose of the point registration module 318 is to apply the refinement transformation 602 to refine the matched result 332 of FIG. 3 from the feature matching module 316. The refinement transformation 602 further improves the quality of results of finding matches between the first point cloud 122 of FIG. 1 and the second point cloud 124 of FIG. 1.

The point registration module 318 can include a function optimization to estimate the refinement transformation 602 to further improve the quality of the results of finding matches between the first point cloud 122 and the second point cloud 124. For example, the point registration module 318 can be implemented using transformation estimations including 3D translation, 3D rotation, 3D scaling, or a combination thereof, for the refinement transformation 602. Also for example, the function optimization can include functions to be minimized using mean Euclidean distances between all points of the first point cloud 122 to closest surfaces as described by the second point cloud 124. The mean Euclidean distances represent to-surface distances, which can be pre-generated and looked up during matching for improved computation efficiency.

Further, for example, the function optimization can be performed via or with a particle swarm optimizer. Yet further, for example, the refinement transformation 602 can possibly be implemented with other transformation types including rigid transformations and affine transformations. Yet further, for example, the refinement transformation 602 can possibly be implemented with other distance metrics including weighted distances and Mahalanobis, other optimization methods including gradient descent and conjugate gradient, or a combination thereof.

The refinement transformation 602 can include a refinement error 604. The refinement error 604 is less than the matching error 524 of FIG. 5. For example, the refinement error 604 can include an MSE approximately greater than or equal to 0.1 mm and approximately less than 2 mm. As a specific example, the refinement transformation 602 can include an MSE of 0.14973 mm.

After a final transformation or the refinement transformation 602 is applied to one of the point clouds 104, the refinement error 604 can be calculated by taking all points from one of the point clouds 104 and finding closest or shortest distances for each of the points to points on the surfaces of the second point cloud 124. Values of the closest distances are then squared and averaged.

It has been found that the partial surface points 342 determined based on the refinement transformation 602 having a mean square error approximately greater than or equal to 0.1 mm and approximately less than 2 mm provides improved accuracy in alignment among the point clouds 104 of FIG. 1.

It has also been found that the partial surface points 342 improves quality of matching the point clouds 104 because the partial surface points 342 are aligned for the key points 326 that are based on the refinement transformation 602 having the refinement error 604 less than the matching error 524.

Figure 7:
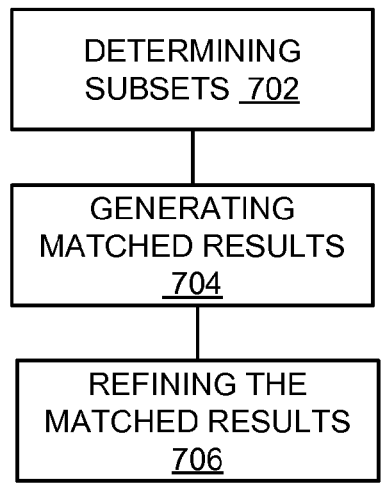
FIG. 7 is a flow chart of a method of operation of an image processing system in a further embodiment of the present invention.

Referring now to FIG. 7, therein is shown a flow chart of a method 700 of operation of an image processing system in a further embodiment of the present invention. The method 700 includes: determining subsets of point clouds, the subsets selected based on key points of a three-dimensional object in a block 702; generating matched results based on a matching transformation of the subsets in a block 704; and refining the matched results based on a refinement transformation to align different data sets of the point clouds for displaying the aligned data sets on a device, wherein the refinement transformation includes a refinement error less than a matching error of the matching transformation in a block 706.

Thus, it has been discovered that the image processing system of the present invention furnishes important and heretofore unknown and unavailable solutions, capabilities, and functional aspects for an image processing system with registration. The resulting method, process, apparatus, device, product, and/or system is straightforward, cost-effective, uncomplicated, highly versatile and effective, can be surprisingly and unobviously implemented by adapting known technologies, and are thus readily suited for efficiently and economically manufacturing image processing systems fully compatible with conventional manufacturing methods or processes and technologies.

Another important aspect of the present invention is that it valuably supports and services the historical trend of reducing costs, simplifying systems, and increasing performance.

These and other valuable aspects of the present invention consequently further the state of the technology to at least the next level.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hithertofore set forth herein or shown in the accompanying drawings are to be interpreted in an illustrative and non-limiting sense.

What is claimed is:

1. A method of operation of an image processing system comprising:
    determining subsets of point clouds, the subsets selected based on key points of a three-dimensional object and selected by removing a point cloud with a relatively flat region;
    generating matched results based on a matching transformation of the subsets; and
    refining the matched results based on a refinement transformation to align different data sets of the point clouds for displaying the aligned data sets on a device, wherein the refinement transformation includes a refinement error less than a matching error of the matching transformation.

2. The method as claimed in claim 1 wherein determining the subsets of the point clouds includes determining the subsets of the point clouds derived from an image source based on an image collocation method.

3. The method as claimed in claim 1 wherein determining the subsets of the point clouds includes determining the subsets of the point clouds derived from an image source based on a volumetric image acquisition method.

4. The method as claimed in claim 1 wherein generating the matched results includes generating the matched results by removing an outlier based on a predetermined model of the three-dimensional object.

5. The method as claimed in claim 1 wherein refining the matched results includes refining the matched results based on the refinement transformation having a mean square error approximately less than 2 millimeters.

6. A method of operation of an image processing system comprising:
    determining subsets of point clouds, the subsets selected based on key points of a three-dimensional object and selected by removing a point cloud with a relatively flat region;
    generating matched results based on a matching transformation of the subsets, the matching transformation includes a rotation transformation; and
    refining the matched results based on a refinement transformation to align different data sets of the point clouds for displaying the aligned data sets on a device, wherein the refinement transformation includes a refinement error less than a matching error of the matching transformation.

7. The method as claimed in claim 6 wherein determining the subsets of the point clouds includes determining the subsets of the point clouds derived from an image source based on an object model generation method.

8. The method as claimed in claim 6 wherein determining the subsets of the point clouds includes determining the subsets of the point clouds derived from an image source based on a surface scanning method.

9. The method as claimed in claim 6 wherein generating the matched results includes generating the matched results by removing an outlier based on a predetermined model of the three-dimensional object and a random sample consensus algorithm.

10. The method as claimed in claim 6 wherein refining the matched results includes refining the matched results based on the refinement transformation having a mean square error approximately greater than or equal to 0.1 millimeters and approximately less than 2 millimeters.

11. An image processing system comprising:
    a feature selection module for determining subsets of point clouds, the subsets selected based on key points of a three-dimensional object and selected by removing a point cloud with a relatively flat region;
    a feature matching module, coupled to the feature selection module, for generating matched results based on a matching transformation of the subsets; and
    a point registration module, coupled to a processor and the feature matching module, for refining the matched results based on a refinement transformation to align different data sets of the point clouds for displaying the aligned data sets on a device, wherein the refinement transformation includes a refinement error less than a matching error of the matching transformation.

12. The system as claimed in claim 11 wherein the feature selection module is for determining the subsets of the point clouds derived from an image source based on an image collocation method.

13. The system as claimed in claim 11 wherein the feature selection module is for determining the subsets of the point clouds derived from an image source based on a volumetric image acquisition method.

14. The system as claimed in claim 11 wherein the feature matching module is for generating the matched results by removing an outlier based on a predetermined model of the three-dimensional object.

15. The system as claimed in claim 11 wherein the point registration module is for refining the matched results based on the refinement transformation having a mean square error approximately less than 2 millimeters.

16. The system as claimed in claim 11 wherein the feature matching module is for generating the matched results based on the matching transformation, the matching transformation includes a rotation transformation.

17. The system as claimed in claim 16 wherein the feature selection module is for determining the subsets of the point clouds derived from an image source based on an object model generation method.

18. The system as claimed in claim 16 wherein the feature selection module is for determining the subsets of the point clouds derived from an image source based on a surface scanning method.

19. The system as claimed in claim 16 wherein the feature matching module is for generating the matched results by removing an outlier based on a predetermined model of the three-dimensional object and a random sample consensus algorithm.

20. The system as claimed in claim 16 wherein the point registration module is for refining the matched results based on the refinement transformation having a mean square error approximately greater than or equal to 0.1 millimeters and approximately less than 2 millimeters.

* * * * *